United States Patent [19]

Messori et al.

[11] 4,275,204
[45] Jun. 23, 1981

[54] PREPARATION OF CHLORO-BIS(ALKYLAMINO)-S-TRIAZINES

[75] Inventors: Vittorio Messori; Renato Francese; Roberto Esposito, all of Turin, Italy

[73] Assignee: Rumianca S.p.A., Turin, Italy

[21] Appl. No.: 73,360

[22] Filed: Sep. 7, 1979

[51] Int. Cl.³ .......................................... C07D 251/50
[52] U.S. Cl. ................................. 544/204; 544/194; 544/218
[58] Field of Search ........................................ 544/204

[56] References Cited

U.S. PATENT DOCUMENTS

| | | | |
|---|---|---|---|
| 3,306,725 | 2/1967 | Knusli et al. | 544/204 |
| 3,639,399 | 2/1972 | Daugherty et al. | 544/204 |
| 4,058,662 | 11/1977 | Haschke et al. | 544/204 |
| 4,099,006 | 7/1978 | Baldi et al. | 544/204 |
| 4,182,874 | 1/1980 | Baldi et al. | 544/204 |
| 4,182,875 | 1/1980 | Francese et al. | 544/204 |

*Primary Examiner*—John D. Randolph
*Attorney, Agent, or Firm*—Sughrue, Rothwell, Mion, Zinn and Macpeak

[57] ABSTRACT

Chloro-bis(alkylamino)-s-triazines are prepared by stepwise replacement of two chlorine atoms of cyanuric chloride by reaction with amines and alkali metal hydroxide in a medium comprising water and a liquid organic compound which is a solvent for cyanuric chloride and is substantially immiscible with water, the first step being carried out by contacting a first amine with a reaction medium containing the cyanuric chloride and the whole of the alkali metal hydroxide used for the step-wise replacement.

9 Claims, No Drawings

PREPARATION OF CHLORO-BIS(ALKYLAMINO)-S-TRIAZINES

The present invention relates to an improved procedure for the preparation of chloro-bis(alkylamino)-s-triazines.

The chloro-bis(alkylamino)-s-triazines are compounds definable by means of the general formula:

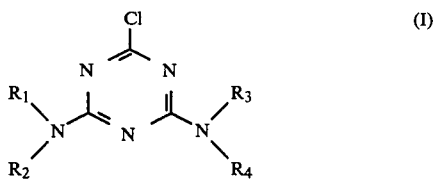

where $R_1$, $R_2$, $R_3$ and $R_4$ independently are hydrogen, an alkyl radical containing from 1 to 5 atoms of carbon, or particular groups of a different nature from the alkyl group.

The chloro-bis(alkylamino)-s-triazines are valued herbicides and the compounds most known belonging to this group are: 2-chloro-4-ethylamino-6-isopropylamino-s-triazine(atrazine), 2-chloro-4,6-bis(ethylamino)-s-triazine (simazine) and 2-chloro-4,6-bis(isopropylamino)-s-triazine (propazine). The herbicidal characteristics of these compounds are described in U.S. Pat. No. 2,891,855 here given as a reference.

The chloro-bis(alkylamino)-s-triazines are generally prepared from cyanuric chloride by step-wise replacement of two atoms of chlorine, as reported, for example, by W. Pearlman and C. K. Banks in J. Am. Chem. Soc. 70, 3726 (1948). In practice the reaction is carried out according to the general scheme:

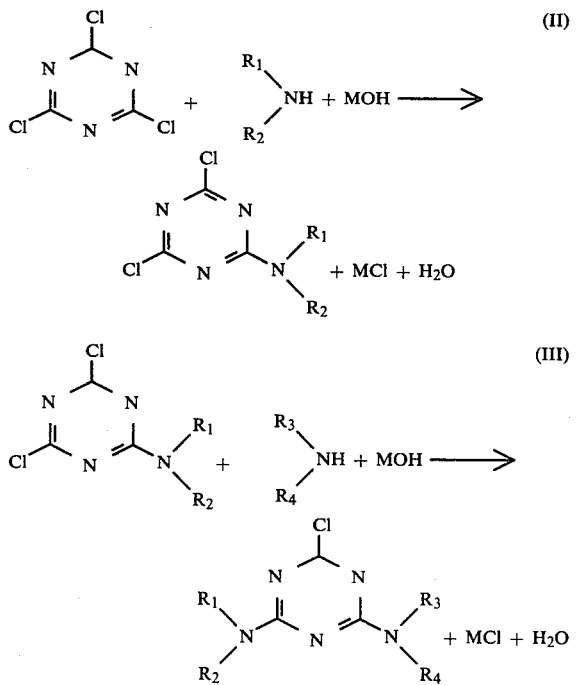

where M represents an alkali metal.

In particular the preparation of atrazine is generally carried out by a discontinuous method, by reacting, in a first reaction stage, cyanuric chloride with isopropylamine in the presence of sodium hydroxide to give 2,4-dichloro-6-isopropylamino-s-triazine. This latter is reacted, in a second stage, with ethylamine and with a further quantity of sodium hydroxide with the subsequent formation of the desired product: 2-chloro-4-ethylamino-6-isopropylamino-s-triazine.

Various ways of carrying out the above reactions (II) and (III) have already been tried in the art, and, in particular, different reaction media have been used to improve the yield and/or quality of the final product. Thus, it has already been proposed to carry out the reactions in the following media:

an aqueous medium containing a surface active agent capable of maintaining the cyanuric chloride in suspension in a finely divided state;

a water-organic compound single phase medium, such as water-acetone, water-dioxan or water-acetonitrile, in which the organic compound is a solvent for the cyanuric chloride and is miscible with water in all proportions;

a water-organic compound two phase medium, such as water-chlorobenzene, water-toluene or water-carbon tetrachloride, in which the organic compound is a solvent for the cyanuric chloride but is substantially immiscible with water;

a water-organic compound two phase medium such as water-methyl ethyl ketone, water-methyl propyl ketone or water-diethyl ketone, in which the organic compound is a solvent for the cyanuric chloride and is only partly miscible with water;

Finally, processes have been described in which the reactions are carried out in a non-aqueous medium.

Whichever reaction medium has been chosen the first reaction stage (reaction II) is usually carried out with a cyanuric chloride: amine: alkali metal hydroxide molar ratio of 1:1:1, while the second stage (reaction III) is carried out with a slight excess of the amine and of the alkali metal hydroxide compared with the stoichiometric value (typically a 3% molar excess) in order to ensure the complete reaction of the intermediate: 2,4-dichloro-6-alkylamino-s-triazine.

In the processes under discussion, the yield of the chloro-bis(alkylamino)-s-triazine and its purity are limited by secondary reactions, such as reactions (IV) and (V) below, and especially by the reaction between the alkali metal hydroxide and the intermediate produced by the substitution of the first chlorine atom in the cyanuric chloride:

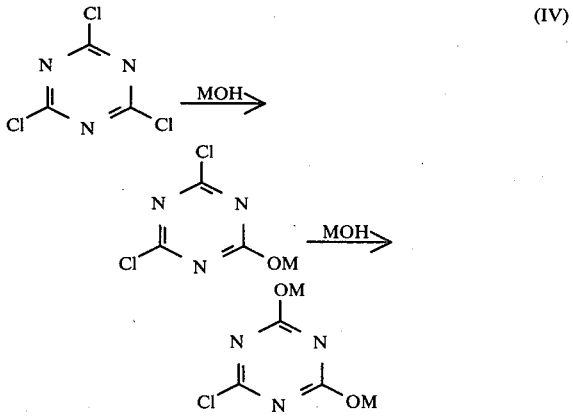

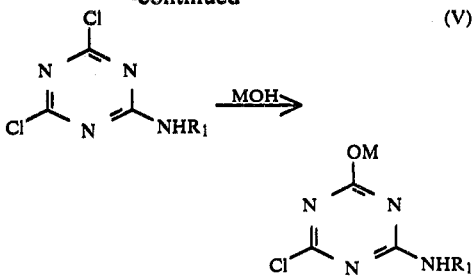

Due to the possible occurrence of these secondary reactions, in the known art, the process for the preparation of a chloro-di(alkylamino)-s-triazine is carried out with reaction mixtures in which the quantity of free alkali metal hydroxide is maintained at negligibly low values at every moment, usually by feeding the alkali metal hydroxide gradually into the reaction mixture containing all the cyanuric chloride and all the amine. Such a method is disclosed for example in U.S. Pat. No. 4,058,662.

Alternatively, equivalent quantities of the amine and of the alkali metal hydroxide are fed gradually into a reaction medium containing all the cyanuric chloride necessary for the reaction. Thus, for example, according to U.S. Pat. No. 4,099,006, the amine and the alkali metal hydroxide are fed gradually at different rates into a reaction medium containing the cyanuric chloride. More specifically, according to this patent, an excess of the amine with respect to the alkali metal hydroxide is maintained in the reaction medium at any moment and good yields of the chloro-di(alkylamino)-s-triazines are achieved with good purity. In particular, this method results in a significant reduction in the formation of the by-products of the secondary reactions of the alkali metal hydroxide with the cyanuric chloride and its first substitution product.

It has now been found possible to increase the yield and the purity of chloro-di(alkylamino)-s-triazines even further by means of an improved process which allows a considerable simplification of the operating procedure.

Thus, the invention provides a process for preparing chloro-bis(alkylamino)-s-triazine by step-wise replacement of two chlorine atoms of cyanuric chloride by means of alkylamino groups in a medium comprising water and a liquid organic compound which is a solvent for cyanuric chloride, by reaction in a first step of a first amine, cyanuric chloride and alkali metal hydroxide in substantially equimolecular amounts and by reaction in a second step of the resulting mono(alkylamino)-s-triazine, a second amine and alkali metal hydroxide in substantially equimolecular amounts, characterized in that said organic compound is substantially immiscible with water and further characterized in that said first step is carried out by contacting said first amine with a reaction medium containing the cyanuric chloride and the whole of the alkali metal hydroxide used for the step-wise replacement.

The present invention is based essentially on the finding that it is possible to avoid, or substantially avoid, the hydrolysis of the cyanuric chloride when carrying out the step-wise reaction in the presence in the beginning of all the alkali metal hydroxide needed for the reaction, and using a two-phase reaction medium of the type described above. This method thus, on the one hand, allows a noticeable simplification of the operating procedure and, on the other hand, allows high reaction yields of the chloro-di(alkylamino)-s-triazines with high purity to be achieved. It is thought that these desirable results stem, at least to some extent, from the presence of the alkali metal hydroxide in the aqueous phase which drastically reduces the solubility in this phase of the alkylamine added to the reaction medium. Hence the amine transfers practically quantitatively into the organic phase and has a beneficial effect both on the rate and on the selectivity of the reaction. Even the alkali metal chloride, which is substituted gradually for the alkali metal hydroxide in the course of the reaction, contributes to reducing the solubility of the alkylamine in the aqueous phase, so that the whole course of the reaction is carried out under conditions which ensure the immediate transfer of the alkylamine into the organic phase as it is added to the reaction medium.

These conditions are not achieved when the step-wise reaction is carried out according to the known methods in which the alkali metal hydroxide, and possibly the alkylamine, is added gradually to the two-phase medium containing the cyanuric chloride. Under these circumstances the alkylamine is distributed between the aqueous and the organic phases and it is only as the reaction proceeds that the fraction present in the aqueous phase migrates into the organic phase.

The organic compounds used in the two-phase system of the process of the present invention should satisfy the following conditions:

no reactivity towards the reagents and the reaction products;

good solvating power for the cyanuric chloride;

water content, under saturation conditions, not exceeding 0.3% and preferably less than 0.1% by weight.

The preferred organic compounds are toluene, xylene, chlorobenzene and carbon tetrachloride.

The insolubility, or negligible solubility, of the water in the organic solvent is also advantageous with regard to the recycling of said solvent after separation from the reaction products. In fact, the solvent may be distilled in the form of an azeotropic mixture with water and recycled after a simple phase separation. It should also be noted that a water content of greater than 0.3% by weight in the organic solvent, under the conditions in which the reaction is carried out, is harmful in that it gives rise to rapid hydrolysis of the cyanuric chloride.

Conveniently, a water/organic compound weight ratio of from 0.2:1 to 0.8:1 is maintained in the two-phase reaction medium.

The other operating conditions do not substantially depart from those conventionally used in the art. Thus, for example, the step-wise reaction may be carried out at a temperature of from 0° to 100° C. The alkali metal hydroxide is preferably sodium hydroxide. The quantity of alkali metal hydroxide is substantially that needed for the formation of the chloro-bis(alkylamino)-s-triazine, and it is generally preferably to use a slight excess of hydroxide (for example up to 5% molar excess) with respect to the quantity stoichiometrically required for the step-wise reaction. Preferably the molar ratio between cyanuric chloride and hydroxide is maintained at a value of from 1:2 to 1:2.05.

The quantity of alkylamine used in the first reaction step is equivalent, or nearly equivalent, to that needed for the formation of the 2,4-dichloro-6-alkylamino-s-triazine intermediate. In the case of a discontinuous process, the temperature is generally maintained at a value not exceeding 60° C. and preferably not exceeding about 25° C. In the case of a continuous method, the temperature is generally maintained at a value not exceeding 90° C. Overpressure is not generally applied, or the overpressure necessary to maintain the reaction medium in the liquid phase is applied. Conveniently the amount of monoalkylamino derivative at the end of the first step is from 10 to 20% by weight with respect to the weight of the chosen organic solvent.

In the second reaction step, it is generally convenient to use a slight molar excess of alkylamine, such as from 1 to 5 molar %, with respect to the quantity stoichiometrically required for the second reaction step, in order to ensure a substantially complete conversion of the mono(alkylamino) derivative. Therefore, the molar ratio between cyanuric chloride and alkylamine used in the two steps is generally from 1:2 to 1:2.05. The second step is generally carried out at a temperature of from 25° to 90–100° C.

Conveniently, the alkylamines used in the first and second reaction steps are fed into the reaction zone in the form of an aqueous solution. The cyanuric chloride is generally fed in the form of a solution in the chosen organic solvent, and the hydroxide in the form of an aqueous solution. The alkylamines used in the process of the invention are preferably monoalkylamines.

The process of the present invention may be carried out continuously or discontinuously. Thus, in the case of the discontinuous preparation of 2-chloro-4-ethylamino-6-isopropylamino-s-triazine (atrazine), the following preferred conditions are used:

the cyanuric chloride and the organic solvent are loaded into a conventional reactor provided with an agitator, the mixture is cooled to a temperature of 0° to 5° C. and aqueous sodium hydroxide (typically 30 wt. % solution) is added in an amount of from 2 to 2.05 moles for every mole of cyanuric chloride;

the mass is maintained under agitation and aqueous isopropylamine is added gradually (preferably in a 70% by weight aqueous solution) in an amount of 1 mole for every mole of cyanuric chloride and the thermal effects are controlled such that the temperature does not exceed about 25° C.;

ethylamine is then added gradually to the agitated mass (preferably in a 50% by weight aqueous solution) in quantities of from 1 to 1.05 moles for every mole of cyanuric chloride introduced initially and the reaction is allowed to proceed to completion, the temperature being maintained below about 55° to 60° C.;

the 2-chloro-4-ethylamino-6-isopropylamino-s-triazine is finally recovered from the reaction products obtained. Wholly similar considerations apply in the case of the other bis(alkylamino)-s-triazines.

The process of the present invention may also be carried out continuously by using two or more cascade reactors or by using tubular reactors. In the latter case, 2-chloro-4-ethylamino-6-isopropylamino-s-triazine may be prepared under the following general conditions:

the cyanuric chloride dissolved in the organic solvent, the isopropylamine and the aqueous sodium hydroxide in a molar ratio of 1:1:2 to 1:1:2.05 are fed to the inlet end of a tubular reactor, the reaction being carried out in the reactor under turbulent conditions, at a temperature not greater than 90° C., until substantially all the cyanuric chloride has been converted to 2,4-dichloro-6-isopropylamino-s-triazine;

the reaction products discharged from the outlet end of the reactor are fed continuously to the inlet end of a second tubular reactor together with one mole, or about one mole (up to 1.05 moles) of monoethylamine for every mole of cyanuric chloride introduced initially, the reaction in the second reactor being again carried out under turbulent conditions and at a temperature not greater than 100° C., until the 2,4-dichloro-6-isopropylamino-s-triazine is substantially completely converted to 2-chloro-4-ethylamino-6-isopropylamino-s-triazine (atrazine) and the reaction products are discharged continuously from the outlet end of the second reactor;

the 2-chloro-4-ethylamino-6-isopropylamino-s-triazine is recovered from the said reaction products. Again wholly similar considerations apply in the case of other bis-(alkylamino)-s-triazines.

The two reaction steps may be carried out in two distinct tubular reactors, as indicated above, or in a single reactor. In the latter case, the cyanuric chloride dissolved in the chosen organic solvent, the aqueous sodium hydroxide and the isopropylamine are fed to the inlet end of the reactor in the quantities indicated above and the monoethylamine is fed to a suitable intermediate position.

It should be noted that a part of the alkylamine feeds may be introduced at various points along the tubular reaction zones, both in the first and the second reaction steps.

According to a preferred embodiment 2-chloro-4-ethylamino-6-isopropylamino-s-triazine is prepared in a tubular reactor, the first replacement step being carried out under isothermal conditions at a temperature of from 30° to 90° C., or under adiabatic conditions with a maximum temperature not greater than 90° C. When the reaction is carried out adiabatically, the inlet temperature of the reagents is not critical in that the reaction is initiated easily even at relatively low temperatures. As regards the second replacment step, this may be carried out under isothermal conditions at a temperature of 40°–50° C. to 100° C. or under adiabatic conditions with a maximum temperature not greater than 100° C.

In every case the organic solvent is distilled from the reaction product, at a pressure equal to or less than atmospheric, in the form of an azeotropic mixture with water. The distillate separates into two phases of which the organic phase is recycled directly to the reaction. The distillation residue consists of a dense suspension of the 2-chloro-4-ethylamino-6-isopropylamino-s-triazine. This suspension is filtered and then the atrazine is recovered by known methods.

By means of the process of the invention there may be prepared all the compounds definable by means of the general formula (I) in which $R_1, R_2, R_3$ and $R_4$ independently are hydrogen, alkyl radicals either the same or different, linear, branched, or cyclic and having from 1 to 5 carbon atoms. Examples of alkyl radicals are: methyl, ethyl, isopropyl, cyclopropyl, n-butyl, sec-butyl and tert-butyl.

In the following examples specific reference will be made to the preparation of 2-chloro-4-ethylamino-6-isopropylamino-s-triazine, but wholly similar considerations apply to the preparation of other chloro-bis(alkylamino)-s-triazines.

EXAMPLE 1

There is used a 2-liter capacity reactor provided with an agitator, a cooling jacket, a thermometer and means for feeding in the reagents.

Initially 184 g (1 mole) of cyanuric chloride in solution in about 500 g of toluene are fed into the reactor. As soon as the temperature has stabilised at 5° C., 273 g of an aqueous solution containing 30% by weight of sodium hydroxide (2.05 moles) are added. No increase in temperature is noted and the pH raises from an initial value of 2-3 to a value of the order to 11.5-12 which is maintained during the course of the subsequent reaction.

After the addition of the aqueous sodium hydroxide, 84 g of an aqueous solution containing 70% by weight of isopropylamine (1 mole) are added under thorough agitation. This addition is carried out gradually over a period of 20-25 minutes, during which time the temperature of the mass rises from 5° C. to about 22-25° C.

At the end of this addition, about 91.5 g of an aqueous solution containing 50% by weight of ethylamine (1.02 moles) are added without interruption and under strong agitation. During this addition the temperature rises from 25° to 50° C. and the final pH is of the order of 11.5-12.

The suspension thus obtained is distilled to recover the toluene.

370 g of water are added to the distillation residue and the mass is filtered at 60° C. The filtered solid is washed with water until the sodium chloride has been completely eliminated.

After drying for ten hours in an oven at 90°-100° C., 2-chloro-4-ethylamino-6-isopropylamino-s-triazine is obtained with a purity of 98% and a yield of 96%.

EXAMPLE 2

The reactions are carried out continuously in a tubular reactor having a total volume of 48 liters and provided with filling bodies. The first 12 liters of the reactor are intended for the replacement of the first chlorine atom in the cyanuric chloride (stage a), the remaining 36 liters being intended for the replacement of the second chlorine atom (stage b).

1317 Kg/hour of a toluene solution containing 14% by weight of cyanuric chloride and 882 Kg/hour of an aqueous solution containing 6.7% by weight of isopropylamine and 9.3% by weight of sodium hydroxide are fed continuously to the inlet end of the reactor. Thus the molar ratio between cyanuric chloride, isopropylamine and sodium hydroxide at the inlet to stage (a) 1:1:2.05.

The reaction of stage (a) is carried out adiabatically with an inlet temperature of 18° C. and an outlet temperature of 60° C.

To the inlet to stage (b) are fed continuously, 90 Kg/hour of an aqueous solution containing 50% by weight of ethylamine (1 K mole). No heat exchange is effected between stages (a) and (b) and the reaction mixture is discharged from the outlet end of the reactor at a temperature of 85° C. 2-chloro-4-ethylamino-6-isopropylamino-s-triazine is separated from the reaction products with a purity of 99% and a yield of about 99%.

EXAMPLE 3

There is used the tubular reactor of Example 2, three separate solutions being fed continuously to the inlet to stage (a), namely 1,317 Kg/hour of a toluene solution containing 14% by weight of cyanuric chloride, 84.4 Kg/hour of an aqueous solution containing 70% by weight of isopropylamine and 273.3 Kg/hour of an aqueous solution containing 30% by weight of sodium hydroxide. Thus the molar ratio between the cyanuric chloride, isopropylamine and sodium hydroxide at the inlet to stage (a) is 1:1:2.05. The temperature at the inlet to stage (a) is 18°-20° C. and a cooling is effected so as to prevent the temperature from rising above about 60°-65° C. at any point of stage (a).

92 Kg/hour of an aqueous solution containing 50% by weight of ethylamine (1.02 Kmoles/hour) are fed to the inlet to stage (b). No heat exchange is effected in stage (b) and the temperature of the reaction mixture at the outlet from this stage is 80° C. 2-chloro-4-ethylamino-6-isopropylamino-s-triazine is separated from this mixture as in Example 1 with a purity of 99% and with a yield of about 99%.

We claim:

1. In a process for preparing chloro-bis(alkylamino)-s-triazine by step-wise replacement of two chlorine atoms of cyanuric chloride by means of alkylamino groups in a medium comprising water and a liquid organic compound which is a solvent for cyanuric chloride, by reaction in a first step of a first amine, cyanuric chloride and alkali metal hydroxide in substantially equimolecular amounts and by reaction in a second step of the resulting mono(alkylamino)-s-triazine, a second amine and alkali metal hydroxide in substantially equimolar amounts, the improvement which comprises using an organic compound which is substantially immiscible with water and carrying out said first step by contacting said first amine with a reaction medium containing the cyanuric chloride and the whole of the alkali metal hydroxide used for the step-wise replacement.

2. The process of claim 1, wherein there is used an organic compound having a water content, under saturation conditions, not exceeding 0.3% by weight.

3. The process of claim 1 wherein the organic compound is selected from the group consisting of toluene, xylene, chlorobenzene and carbon tetrachloride.

4. The process of claim 1, wherein the step-wise replacement is carried out at a temperature of from 0° to 100° C.

5. The process of claim 1, wherein the molar ratio between cyanuric chloride and alkali metal hydroxide is from 1:2 to 1:2.05.

6. The process of claim 1, wherein there is maintained a weight ratio of from 0.2:1 to 0.8:1 between the water and the organic compound in the reaction medium.

7. The process of claim 1, wherein the alkali metal hydroxide is sodium hydroxide.

8. The process of claim 1, wherein said second amine is used in a molar excess not exceeding 5% with respect to the stoichiometrical value in said second step.

9. The process of claim 1, wherein said first amine is isopropylamine and said second amine is monoethylamine.

* * * * *